(12) United States Patent
Wang et al.

(10) Patent No.: US 8,889,823 B2
(45) Date of Patent: Nov. 18, 2014

(54) METHOD TO MAKE POLY(L-LACTIDE) STENT WITH TUNABLE DEGRADATION RATE

(75) Inventors: Yunbing Wang, Sunnyvale, CA (US); Xiao Ma, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 421 days.

(21) Appl. No.: 12/751,773

(22) Filed: Mar. 31, 2010

(65) Prior Publication Data

US 2011/0021717 A1 Jan. 27, 2011

Related U.S. Application Data

(63) Continuation-in-part of application No. 12/506,973, filed on Jul. 21, 2009.

(51) Int. Cl.
*C08G 63/08* (2006.01)
*A61L 31/14* (2006.01)
*A61L 31/06* (2006.01)
*C08G 63/90* (2006.01)

(52) U.S. Cl.
CPC .............. *C08G 63/90* (2013.01); *A61L 31/148* (2013.01); *C08G 63/08* (2013.01); *A61L 31/06* (2013.01)
USPC ........... 528/354; 424/423; 525/408; 525/411; 525/413; 525/415; 525/461

(58) Field of Classification Search
USPC .......... 424/423; 525/408, 411, 413, 415, 461; 528/354
See application file for complete search history.

(56) References Cited

U.S. PATENT DOCUMENTS

| | | | |
|---|---|---|---|
| 4,539,981 A | 9/1985 | Tunc | |
| 5,747,637 A * | 5/1998 | Shinoda et al. | 528/354 |
| 5,824,059 A | 10/1998 | Wijay | |
| 6,121,410 A | 9/2000 | Gruber et al. | |
| 6,716,957 B2 | 4/2004 | Tunc | |
| 7,070,615 B1 | 7/2006 | Igaki | |
| 7,291,166 B2 | 11/2007 | Cheng et al. | |
| 7,524,891 B2 | 4/2009 | Rose et al. | |
| 7,553,325 B2 | 6/2009 | Stinson | |
| 2003/0069629 A1 | 4/2003 | Jadhav et al. | |
| 2004/0138333 A1 | 7/2004 | Kim et al. | |
| 2006/0246108 A1* | 11/2006 | Pacetti et al. | 424/426 |
| 2007/0179276 A1 | 8/2007 | Krul et al. | |
| 2007/0253999 A1 | 11/2007 | Huang et al. | |
| 2007/0282435 A1 | 12/2007 | Wang et al. | |
| 2009/0182404 A1 | 7/2009 | Shokoohi | |
| 2010/0262224 A1 | 10/2010 | Kleiner | |

FOREIGN PATENT DOCUMENTS

| | | |
|---|---|---|
| EP | 1 184 008 | 3/2002 |
| JP | H8-89567 | 4/1996 |
| JP | 2008-063420 | * 3/2008 |
| WO | WO 01/67990 | 9/2001 |
| WO | WO 2007/146354 | 12/2007 |
| WO | WO 2008045516 | * 5/2008 |

OTHER PUBLICATIONS

International Search Report for PCT/US2011/025074, mailed May 31, 2011, 14 pgs.
Tammela et al., "Biodegradable urethral stents", BJU International 92, pp. 843-850 (2003).
Hyon et al., "Effects of residual monomer on the degradation of DL-lactide polymer", Polymer Int. vol. 46, No. 3, pp. 196-202, Abstract 1 pg. (1998).
Nakamura et al., "Bioabsorption of polylactides with different molecular properties", J. of Biomed. Mat. Res. vol. 23 pp. 1115-1129 (1989).
Pitt et al., "Aliphatic polyesters. I. The degradation of Poly(e-caprolactone) in Vivo", J. of Applied Pol. Science 26, pp. 3779-3787 (1981).
Pitt et al., "Aliphatic polyesters. II. The degradation of poly (DL-lactide), poly(e-caprolactone), and their copolymers in vivo", Biomaterials 2, pp. 215-220 (1981).
Weir et al., "Degradation of poly-L-lactide. Part I: in vitro and in vivo physiological temperature degradation", J. of Engineering in Medicine 218, pp. 307-319 (2004).
Weir et al., "Degradation of poly-L-lactide. Part 2: Increased temperature accelerated degradation", J. of Eng. In Medicine 218, pp. 321-330 (2004).
International Search Report for PCT/US2010/041998, mailed Feb. 10, 2011, 6 pgs.
Bendix "Chemical synthesis of polylactide and its copolymers for medical applications", Pol. Degrad. and Stability 59, pp. 129-135 (1998).
Notice of Reason for Rejection from JPO for appl. No. JP 2012-521678, dispatched Aug. 26, 2014, 2 pgs.
Translation of the Notice of Reason for Rejection from JPO for appl. No. JP 2012-521678, dispatched Aug. 26, 2014, 2 pgs.

* cited by examiner

*Primary Examiner* — Gregory Listvoyb
(74) *Attorney, Agent, or Firm* — Squire Patton Boggs (US) LLP

(57) ABSTRACT

Methods of making a biodegradable polymeric stent made from poly(L-lactide) and a low concentration of L-lactide monomer is disclosed. The concentration of L-lactide is adjusted to provide a degradation behavior that is suitable for different treatment applications including coronary, peripheral, and nasal. Methods include making a poly(L-lactide) material for a stent with uniformly distributed L-lactide monomer through control of polymerization conditions during PLLA synthesis, control of post-processing conditions, or both.

13 Claims, 4 Drawing Sheets

METHOD TO MAKE POLY(L-LACTIDE) STENT WITH TUNABLE DEGRADATION RATE

CROSS-REFERENCE

This is a continuation-in-part of application Ser. No. 12/506,973 filed on Jul. 21, 2009 and is incorporated by reference herein.

BACKGROUND OF THE INVENTION

1. Field of the Invention

This invention relates to methods of treatment of blood vessels with bioabsorbable polymeric medical devices, in particular, stents.

2. Description of the State of the Art

This invention relates to radially expandable endoprosthesis, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must have sufficient radial strength so that it is capable of withstanding the structural loads, namely radial compressive forces, imposed on the stent as it supports the walls of a vessel. Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents made from biostable or non-erodible materials, such as metals, have become the standard of care for percutaneous coronary intervention (PCI) as well as in peripheral applications, such as the superficial femoral artery (SFA), since such stents have been shown to be capable of preventing early and later recoil and restenosis.

In order not to affect healing of a diseased blood vessel, the presence of the stent is necessary only for a limited period of time. There are certain disadvantages to the presence of a permanent implant in a vessel such as compliance mismatch between the stent and vessel and risk of embolic events. To alleviate such disadvantages, stent can be made from materials that erode or disintegrate through exposure to conditions within the body. Thus, erodible portions of the stent can disappear from the implant region after the treatment is completed, leaving a healed vessel. Stents fabricated from biodegradable, bioabsorbable, and/or bioerodible materials such as bioabsorbable polymers can be designed to completely erode only after the clinical need for them has ended.

Like a durable stent, a biodegradable stent must meet time dependent mechanical requirements. For example, it must provide patency for a minimum time period. However, it is also important for a biodegradable stent to completely degrade from the implant site with in a certain period of time. A biodegradable material that can provide the mechanical requirements may not possess the requisite or desired degradation time. In addition, the requisite or desired degradation time varies between types of applications, i.e. coronary or peripheral.

SUMMARY OF THE INVENTION

Various embodiments of the present invention include a method of fabricating a stent comprising: making PLLA polymer material with a polymerization reaction of LLA monomers, wherein the PLLA polymer material has an LLA monomer content of greater than 4 wt %; processing the PLLA polymer material to reduce the LLA monomer content to no more than 2 wt % and making a polymeric stent body from the processed PLLA.

Additional embodiments of the present invention include a method of fabricating a stent comprising: obtaining a PLLA polymer material having an LLA monomer content of greater than 4 wt %; processing the PLLA polymer to reduce the monomer content to no more than 2 wt %; and making a polymeric stent body from the processed PLLA.

Other embodiments of the present invention include a method of fabricating a stent comprising: making a PLLA polymer material with a polymerization reaction of LLA monomer, wherein the PLLA polymer material has a LLA monomer content of less than 0.5 wt %; increasing the reaction temperature of the PLLA polymer material to cause depolymerization which increases the monomer content to a target LLA monomer content of between 0.5 to 2 wt % of the PLLA; and making a stent body from the PLLA polymer material with the increased monomer content.

Further embodiments of the present invention include a method of making a stent comprising: selecting a reaction temperature between 120-180° C. of a polymerization reaction of LLA monomer to PLLA; selecting a target LLA monomer content for PLLA polymer material from the polymerization reaction between 0.5 to 2 wt %; performing the polymerization reaction for different reaction times to determine a target reaction time that provides a PLLA polymer material with the target LLA monomer content; making the PLLA polymer material with the target LLA monomer content from the polymerization reaction at the target reaction temperature for the target reaction time; and making a stent from the PLLA polymer material with the target LLA monomer.

Additional embodiments of the present invention include a method of making a stent comprising: selecting a reaction time between 1-100 h of a polymerization reaction of LLA monomer to PLLA; selecting a target monomer content of PLLA polymer material from the polymerization reaction between 0.5 to 2 wt %; performing the polymerization reaction for different reaction temperatures between 120-180° C. to determine a target reaction temperature that provides the target LLA monomer content; making the PLLA polymer material with the target LLA monomer content from the polymerization reaction at the target reaction temperature for the target reaction time; and making a stent from the PLLA polymer material with the target monomer content.

DETAILED DESCRIPTION OF THE INVENTION

Coronary arteries refer generally to arteries that branch off the aorta to supply the heart muscle with oxygenated blood. Peripheral arteries refer generally to blood vessels outside the heart and brain.

In both coronary artery disease and peripheral artery disease, the arteries become hardened and narrowed or stenotic and restrict blood flow. In the case of the coronary arteries, blood flow is restricted to the heart, while in the peripheral arteries blood flow is restricted leading to the kidneys, stomach, arms, legs, and feet. The narrowing is caused by the buildup of cholesterol and other material, called plaque, on the inner walls of the vessel. Such narrowed or stenotic portions are often referred to as lesions. Artery disease also includes the reoccurrence of stenosis or restenosis that occurs after an angioplasty treatment. Although there are probably several mechanisms that lead to restenosis of arteries, an important one is the inflammatory response, which induces tissue proliferation around an angioplasty site. The inflammatory response can be caused by the balloon expansion used to open the vessel, or if a stent is placed, by the foreign material of the stent itself.

Embodiments of the present invention are applicable to treatment of coronary and peripheral disease in coronary arteries and various peripheral vessels including the superficial femoral artery, the iliac artery, and carotid artery. The embodiments are further applicable to various stent types, such as self-expandable and balloon expandable stents. The embodiments are further applicable to various stent designs including scaffolding structures formed from tubes, wire structures, and woven mesh structures.

In embodiments of the present invention, a stent includes a plurality of cylindrical rings connected or coupled with linking elements. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are non-load bearing, serving to maintain connectivity between the rings. For example, a stent may include a scaffolding composed of a pattern or network of interconnecting structural elements or struts.

Figure 1:
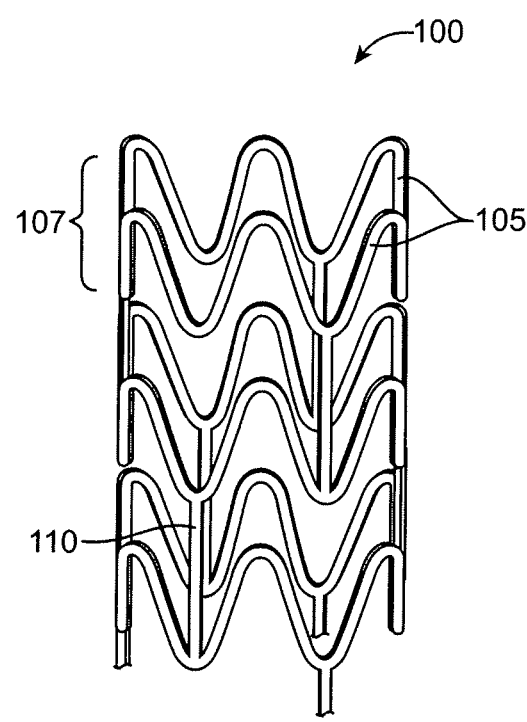
FIG. 1 depicts an exemplary stent.

FIG. 1 depicts a view of an exemplary stent 100. In some embodiments, a stent may include a body, backbone, or scaffolding having a pattern or network of interconnecting structural elements 105. Stent 100 may be formed from a tube (not shown). FIG. 1 illustrates features that are typical to many stent patterns including cylindrical rings 107 connected by linking elements 110. As mentioned above, the cylindrical rings are load bearing in that they provide radially directed force to support the walls of a vessel. The linking elements generally function to hold the cylindrical rings together.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped on to a balloon or catheter for delivery into a bodily lumen.

The prevailing mechanism of degradation of biodegradable polymers is chemical hydrolysis of the hydrolytically unstable backbone. In a bulk eroding polymer, polymer is chemically degraded and material is lost from the entire polymer volume. As the polymer degrades, the molecular weight decreases. The reduction in molecular weight is followed by a reduction in mechanical properties, and then erosion or mass loss. The decrease in mechanical properties eventually results in loss of mechanical integrity demonstrated by fragmentation of the device. Enzymatic attack and metabolization of the fragments occurs, resulting in a rapid loss of polymer mass.

The treatment of artery disease with a stent of the present invention has time dependent properties once it is implanted which enable the treatment and healing of a diseased section of the vessel. In particular, the molecular weight, the mechanical properties, the mechanical integrity, and mass change with time. After deployment at a diseased section artery, the stent supports the section at an increased diameter for a period of time. Due to a decrease in molecular weight, the radial strength degrades to the point that the stent can no longer support the walls of the section of the vessel. "Radial strength" of a stent is defined as the pressure at which a stent experiences irrecoverable deformation. The loss of radial strength is followed by a gradual decline of mechanical integrity.

Mechanical integrity refers to the size, shape, and connectivity of the structural elements of the stent. For example, the shape refers to the generally tubular shape of the stent formed by the cylindrically-shape rings connected by the linking elements of the pattern. Mechanical integrity starts to be lost when fractures appear or propagate in structural elements of the stent due to chemical degradation (molecular weight decline). Further loss of mechanical integrity occurs when there is breaking or loss of connectivity in structural elements.

The initial clinical need for any stent is to provide mechanical support to maintain patency or keep a vessel open at or near the deployment diameter. The patency provided by the stent allows the stented segment of the vessel to undergo positive remodeling at the increased deployed diameter. By maintaining the patency of the stented segment at this stage, the stent prevents negative remodeling. Remodeling refers generally to structural changes in the vessel wall that enhance its load-bearing ability so that the vessel wall in the stented section can maintain an increased diameter in the absence of the stent support. A period of patency is required in order to obtain permanent positive remodeling.

During this time period, the stent inhibits or prevents the natural pulsatile function of the vessel. The stent structure prevents recoil and maintains a circular lumen while the vessel remodels and molds itself to the stented diameter, which corresponds to positive remodeling. Early recoil before sufficient modeling takes place can result in negative remodeling, referring to molding of the stent to a diameter significantly less than the original stented diameter, for example, 50% or less than the original deployment diameter.

As the polymer of the stent degrades, the radial strength of the stent decreases and the load of the vessel is gradually transferred from the stent to the remodeled vessel wall. Remodeling of the vessel wall continues after loss of radial strength of the stent. Before the stent loses mechanical integrity, it is desirable for the stent structural elements to become incorporated in the vessel wall by an endothelial layer. The stent then breaks apart which allows vasomotion. The vessel wall continues to remodel as the vessel moves due to vasomotion. The stent eventually erodes away completely leaving a healed vessel with an increased diameter and which can exhibit vasomotion the same or similar to a healthy vessel section.

Poly(L-lactide) (PLLA) is attractive as a stent material due to its relatively high strength and a rigidity at human body temperature, about 37° C. Since it has glass transition temperature between about 60 and 65° C. (Medical Plastics and Biomaterials Magazine, March 1998), it remains stiff and rigid at human body temperature. This property facilitates the ability of a stent to maintain a lumen at or near a deployed diameter without significant recoil.

PLLA has an in vitro degradation time of up to 3 years (Medical Plastics and Biomaterials Magazine, March 1998; Medical Device Manufacturing & Technology 2005). The degradation time is the time required for complete loss of mass of a polymer construct, such as a stent. The degradation time in vivo is shorter and depends on the animal model. In addition to an erosion profile, a PLLA stent has associated molecular weight and mechanical property (e.g., strength) profiles. As demonstrated above, the time dependence of the mechanical properties and mechanical integrity are important in the treatment of a diseased vessel. The degradation properties of PLLA do not generally coincide with what is required or desired for a particular treatment application. For example, it is desirable for a PLLA stent to have a degradation time of about two years (e.g., 22 to 26 months) for coronary vascular application, of about eighteen months (e.g., 16-20 months) for a peripheral application (e.g., superficial femoral artery (SFA)), and less than a year for nasal applications. For coronary and peripheral applications, the radial strength should be maintained for between one to six months, wherein maintaining radial strength refers to the ability of the stent to maintain the stented section at a diameter at least 50% of the original deployed diameter. For coronary and peripheral applications, the start of the loss of mechanical integrity should not occur until at least between 2 and 4 months, where the start of the loss of mechanical integrity corresponds to breaking apart of structural elements.

It is desirable to adapt a PLLA stent to various applications, so that it has the degradation behavior appropriate to each application, without significantly changing the composition of the stent. The embodiments of the present invention relate to adjusting the time-dependent degradation behavior of a PLLA stent through inclusion L-lactide (LLA) monomer in a stent body composed of PLLA.

The embodiments of the stent can include a body or scaffolding that is composed of PLLA with a targeted small amount of LLA monomer. The body can be composed of targeted amount of LLA and the rest of the body can be 100% PLLA. Additionally, the body can be made of the targeted amount of LLA, additional components, and the rest of the body 100% PLLA. The body can be 95 wt % or greater and the rest of the body can be the targeted amount of LLA and optionally the additional components. The additional components can be drugs, polymers, or filler materials such as bioceramic particles. The present invention includes embodiments that exclude additional components or exclude one or more of the additional components mentioned above.

In additional embodiments, the PLLA stent body can include additionally or alternatively, d-lactide, meso-lactide, glycolide, lactic acid, or their oligomers with an Mn less than 1,000 g/mol. The concentration of these additional monomers can be the same as those disclosed for L-lactide.

The stent can further include a coating over the body or scaffolding. In one embodiment, the coating can be a polymer and drug mixture. For example, the coating can be poly(D,L-lactide) and the drug could be an antiproliferative such as everolimus. The coating can be free of the LLA monomer other than incidental migration or diffusion of LLA into the coating.

Low molecular weight PLLA oligomers can also increase the degradation rate, and thus adjust degradation behavior. However, the increase is primarily due to acidic end groups that act as catalysts to increase degradation rate of the PLLA. Thus, the larger the oligomer, a higher the weight fraction of oligomer in the PLLA that is required. Therefore, a much lower weight fraction of LLA monomer than given oligomer is required for a similar effect as the oligomer. The high weight fraction of oligomer can negatively impact the mechanical properties of the stent.

The qualitative and precise effect of LLA monomers on PLLA degradation behavior is not known. For example, the amount of monomer required to obtain desired degradation behavior is not. This can be at least partially attributed to the fact that the degradation behavior of a stent made from a semicrystalline degradable polyester, such as PLLA, is a complex function of several properties of the material and stent body. These properties include the intrinsic hydrolysis rate of the polymer (i.e., the chain scission reactions of the polymer backbone), the degree of crystallinity, the morphology (size and distribution of crystallite domains in the amorphous matrix), molecular weight (as measured by the inherent viscosity, number or weight average molecular weight), and stent body parameters (pattern, strut dimensions and the surface to volume ratio).

A semicrystalline polymer generally may have insufficient strength and fracture toughness to provide adequate and safe treatment of a blood vessel. The fabrication of the stent of present invention includes processing which increases the strength and fracture toughness of the final stent product. This processing provides certain characteristics that affect the degradation behavior, e.g., crystallinity, morphology. The strength and fracture toughness are increased by induced biaxial orientation of polymers in the hoop or circumferential and/or axial direction, a particular range of the degree of crystallinity, and small dispersed crystallites.

The stent is made from an extruded PLLA polymer tube that has been radially expanded and axially stretched to provide the induced orientation. The polymer tube is expanded by blow molding with a percent radial expansion between 200% and 500%, and a percent axial stretch from 20% to 200%. The extruded PLLA tubing has a percent of axial stretch from 100% to 400%. The stent is formed from the expanded tube by laser cutting the tubing in its expanded state.

Additionally, the blow molding process is performed in a manner that results in small crystallites dispersed through an amorphous matrix. Prior to expansion, the tube is heated to a temperature between 70° C. and 95° C. to induce formation of smaller crystallites that enhance fracture toughness. The tube is quenched below the glass transition temperature (Tg) after expansion to prevent further crystal growth. The degree of crystallinity is 30-50%. Below 30% crystallinity the stent body may not be have sufficient strength, while above 50% crystallinity the stent body may be too brittle. The number average molecular weight (Mn) of scaffolding material in the final product (in g/mol) is between 60,000 and 300,000, or more narrowly between 80,000 and 200,000.

An exemplary strut cross-section can be rectangular, for example, 140×140 μm to 160×160 μm or having a cross-sectional area between 20,000 and 25,000 μm².

In one embodiment of the present invention, the stent is composed of PLLA and less than 1 wt % of LLA monomer. In a more preferred embodiment of the present invention the stent includes less than 0.9 wt %, less than 0.7 wt %, less than 0.5 wt %, less than 0.4 wt %, less than 0.3 wt %, less than 0.2 wt %, or less than 0.1 wt % of LLA monomer. In other embodiments, the stent has between 0 and 1 wt % LLA, 1-2 wt % LLA, 2-3 wt % LLA, 3-4 wt % LLA. However, as shown below, it is expected that an LLA content of greater than 1 wt % or greater than 2 wt % will result in a stent that does not maintain radial strength and mechanical strength long enough for effective treatment of a diseased section of a vessel.

The LLA monomer can be dispersed in the form of a powder or particular particles through all or a portion of a stent body. The size of such particles can be less than 100 nm, between 100 nm and 200 nm, or greater than 200 nm, where size can refer to diameter or some other characteristic length. Alternatively, the LLA monomer can be mixed or dissolved on a molecular level with the PLLA.

It has been observed from in vitro and in vivo degradation studies of PLLA stents with L-lactide monomer, discussed below, that LLA provides a dramatic and unexpected increase in the degradation rate of the stent, particularly above about 1 wt %. Stents having monomer compositions above about 1 wt % LLA lose mechanical strength, lose mechanical integrity, and erode away in a fast way. Additionally, the low concentration of LLA are advantageous since the effect of the dispersed monomer in the polymer has no or a minimal effect on the mechanical properties of the polymer.

Additionally, it is important that the LLA monomer be uniformly or substantially uniformly dispersed through the PLLA of the stent to provide uniform degradation behavior through the body of the stent. It has been observed that for such low concentrations of LLA monomer, the uniformity of distribution is highly dependent on the manner of mixing or dispersing of the LLA. Thus, additional embodiments include a method of mixing the LLA in the PLLA stent material.

In vitro and in vivo studies of degradation behavior can be used to assess the influence of LLA monomer concentration on the degradation behavior of a PLLA stent. In addition, the influence can be assessed using theoretical models.

A hydrolytic degradation model for aliphatic polyesters having the form $Mn(t) = Mn(0)\exp(-Kt)$, wherein $Mn(t)$ is the number average molecular weight at time t, $Mn(0)$ is the number average molecular weight at t=0, and K is the hydrolytic degradation rate constant. Pitt, C. G., J. of Applied Polymer Science 26, 3779-3787 (1981); Pitt, C. G., Biomaterials 2, 215-220 (1981); Weir, N. A., Proceedings of the Institution of Mechanical Engineers, Part H: J. of Engineering in Medicine 218, 307-319 (2004); Weir, N. A., Part H: J. of Engineering in Medicine 218, 321-330 (2004). The assumptions inherent in the model are reasonable provided that the mass loss has not occurred, since mass loss would affect the concentrations of water and carboxylic end groups in the sample. The equation can also be written as: $\ln[Mn(t)/Mn(0)] = -Kt$. Therefore, by representing data for $Mn(t)/Mn(0)$ versus t on a log-linear plot, one may infer the hydrolytic degradation rate from the slope of the connecting points.

In vitro and in vivo degradation data has been generated for PLLA stents with different concentrations of LLA monomer to investigate its effect on the degradation behavior of a PLLA stent. The in vivo data was obtained using an animal model. Parameters and behavior that have been monitored include Mn, radial strength, appearance of cracks or fractures in stent struts (structural/mechanical integrity), and degradation time. In all studies, the stent is processed as described herein. The parameters of the stents are shown in Table 1 below. The stents included a coating over a scaffolding composed of poly(DL-lactide) and Everolimus.

TABLE 1

Summary stent parameters in degradation studies

| Specification | Value |
|---|---|
| Backbone polymer (PLLA) | |
| Mw | 180,000-200,000 |
| Mn | 90,000-100,000 |
| Mass of stent (18 mm length) | 9.0 mg |
| Mass/unit length | 0.5 mg/mm |
| Crystallinity | 45% (as measured by DSC) |
| Strut cross section | 150 micron × 150 micron |
| Coating thickness | 3 microns |
| Coating mass | 308 μg (1:1 polymer:Everolimus) |
| Coating polymer | |
| Mw | 66,000 |
| Mn | 39,000 |
| Blow molding: | |
| Percent radial expansion | 400% |
| Percent axial elongation | 20% |
| Laser machining | 120 fs laser |

The in vitro studies were performed in a phosphate buffered saline (PBS buffer) solution at 37° C. The Mn of the stent was measured by GPC using polystyrene standards. The animal model for the in vivo studies was Yucatan mini swine.

In the in vitro study, the Mn dependence on time is plotted in the form of $\ln[Mn(t)/Mn(0)]$ versus time to assess the predictive ability of the hydrolytic degradation model. The model is then used to assess the effect of LLA on the degradation of PLLA.

Figure 2:
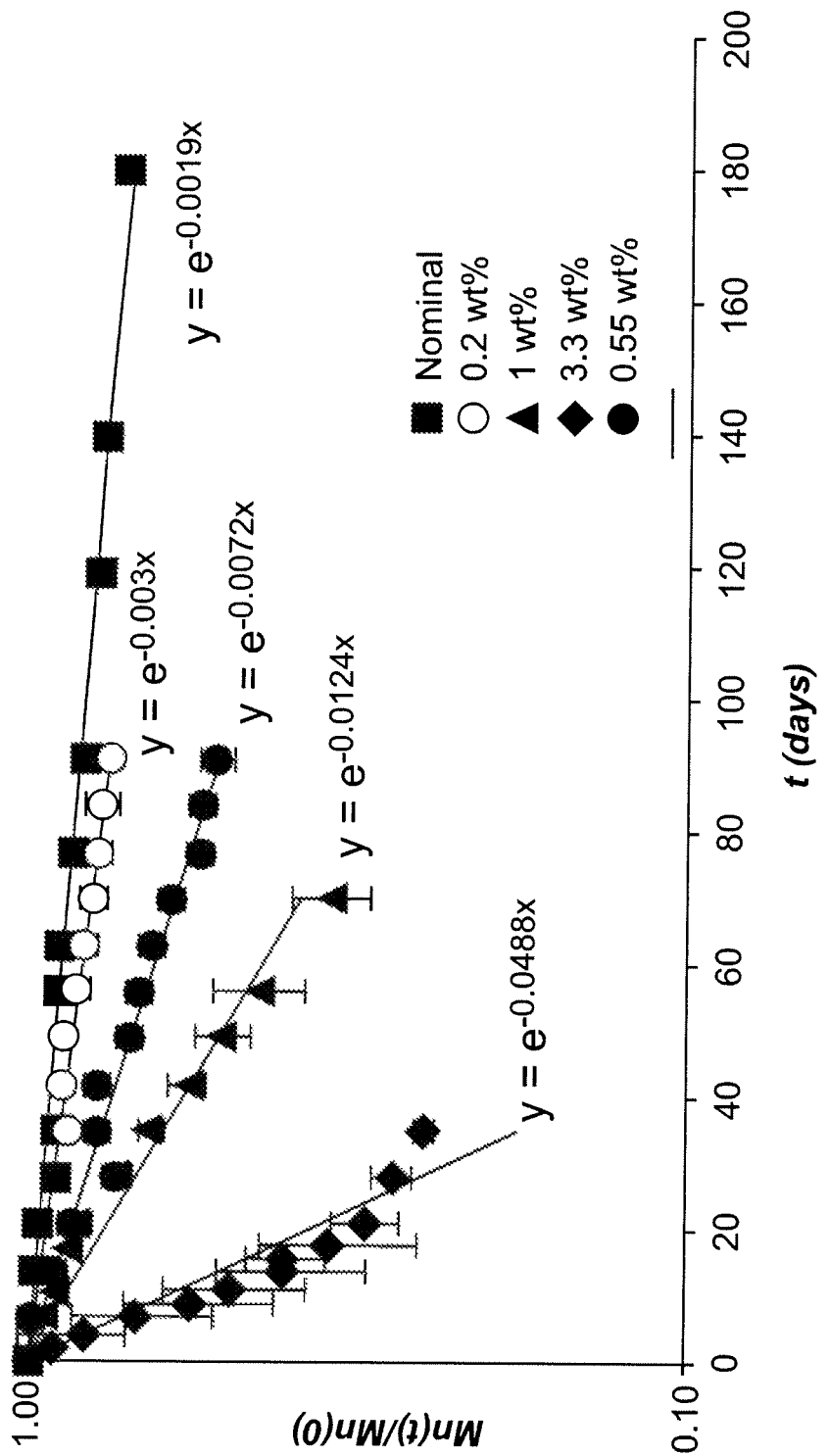
FIG. 2 depicts a plot of the in vitro degradation behavior for a PLLA stent with different concentrations of L-lactide monomer.

In the in vitro studies, the Mn as a function of time was also measured for PLLA stents having different concentrations of LLA monomer. In these studies, the LLA monomer was added to the PLLA resin in a manner described herein. FIG. 2 depicts a plot of ln $[Mn(t)/Mn(0)]$ versus time for this set for four groups of stents: nominal (0.05 wt % LLA), 0.2 wt % LLA, 0.55 wt % LLA, 1 wt % LLA, and 3.3 wt % LLA monomer in PLLA.

Figure 3:
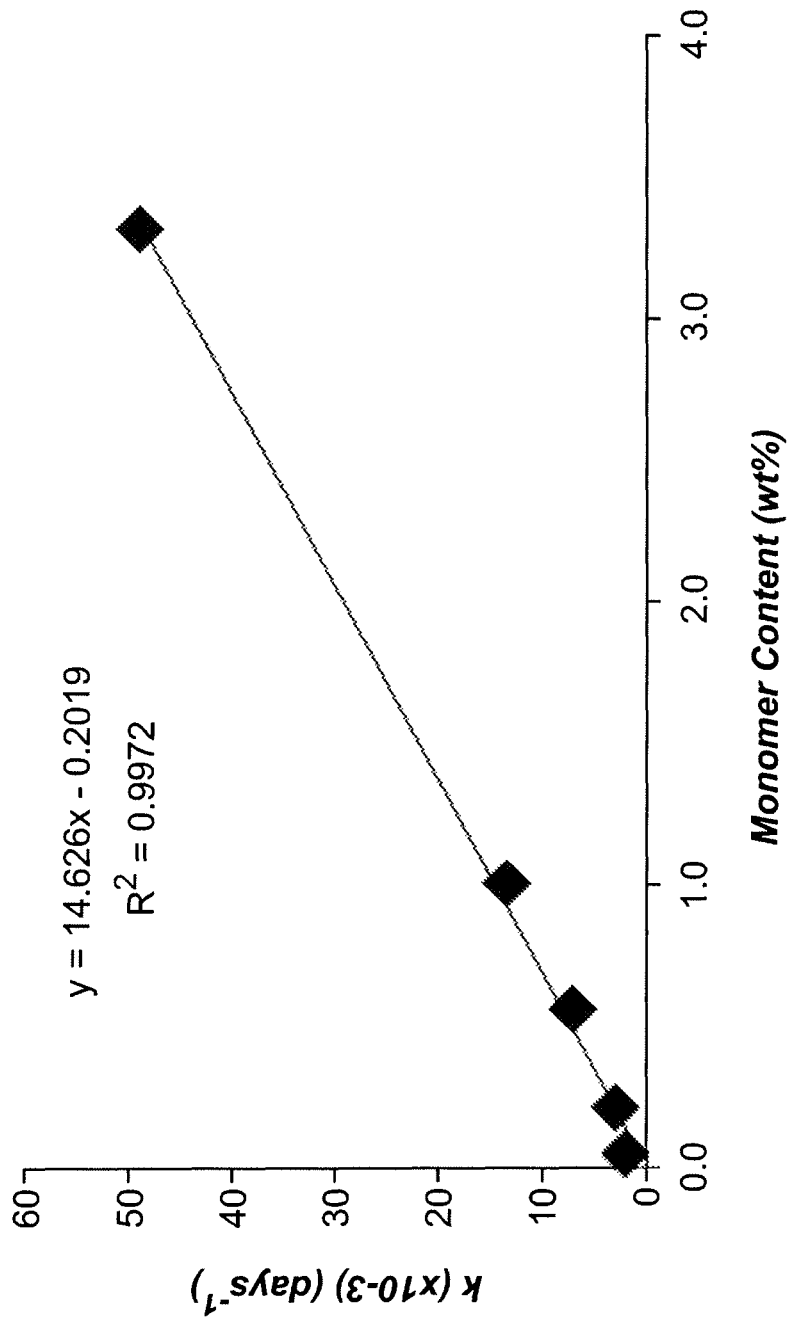
FIG. 3 depicts a plot of a degradation rate constants versus L-lactide monomer concentration based on the data of FIG. 2.

The data for each concentration is fitted with a straight line, the slope of which provides the rate constant, K, of the degradation model. The rate constant, K, for each concentration of LLA monomer is summarized in Table 2 and FIG. 3.

TABLE 2

Rate constant K for degradation model from in vitro data.

| Stent Group: wt % LLA | k (× $10^3$) (days$^{-1}$) | R2 |
|---|---|---|
| Nominal | 1.9 | 0.962 |
| 0.2 | 3.0 | 0.972 |
| 0.55 | 7.2 | 0.969 |
| 1 | 13.4 | 0.960 |
| 3.3 | 48.8 | 0.989 |

The coefficient of determination, R2, is given for each group of data to assess the predictability of the linear degradation model. The closer R2 is to 1, the more reliable the predictive ability of the model. The data in Table 2 shows an unexpectedly dramatic effect of LLA monomer content on the degradation of the stent. For example, when the LLA concentration increases from near 0 to 0.55 wt %, K increases near three times and from near 0 to 1 wt %, the rate constant increases near six times. The differences in the change in the molecular weight with time as the LLA concentration increases is just as dramatic.

Table 3 shows the percent drop in Mn and the Mn at time points based on the model predictions for 1 wt % LLA for the second set of data.

TABLE 3

Change in molecular weight with time for PLLA with 1 wt % PLLA

| Days | Drop in Mn | Mn |
|---|---|---|
| 20 | 23% | 77k |
| 40 | 41% | 59k |
| 60 | 55% | 45k |
| 80 | 65% | 35k |
| 120 | 80% | 20k |

As indicated above, the loss of mechanical integrity starts before mass loss. In addition, the loss of radial strength occurs before or along with loss of mechanical integrity. At the entanglement molecular weight, about 17,000, the polymer no longer has mechanical properties and disintegrates under a applied load. The stent loses mechanical integrity well before the entanglement molecular weight.

As indicated above, the in vitro start of mass loss is expected to be an upper limit for in vivo degradation, that is, mass loss starts at an earlier time in vivo. In addition, the start of mechanical integrity loss and the loss of radial strength might also occur at an earlier time in vivo than in vitro. Table 4 shows in vivo and in vitro data for mass loss for a PLLA stent with no LLA monomer. The difference in the time that mass loss starts and the difference in the degree of loss is significant.

TABLE 4

Comparison of in vitro and in vivo mass loss for PLLA stent with no LLA monomer.

| Time (months) | In vitro mass loss | In vivo Mass loss |
|---|---|---|
| 9 | 0% | 20% |
| 12 | 0% | 30% |
| 18 | — | 35% |
| 21 | 9% | — |

For coronary and peripheral applications, it is believed that the mechanical integrity should remain intact for at least 2 to 4 months without severe fractures (e.g, breaking of struts) after implantation to allow incorporation of stent into vessel wall. Additionally, it is believed that radial strength should be maintained for at least about 1 month to prevent negative remodeling. The radial strength is expected to be lost prior to the mechanical integrity and the start of the loss of mechanical integrity is expected to start before mass loss. A prelude to the start of the loss of mechanical integrity corresponds to the formation of cracks in the stent. Therefore, based on this in vitro data, the LLA concentration should be less than 1 wt % for the stent to maintain radial strength and mechanical integrity for the desired times for coronary and peripheral applications.

In another set of in vitro studies, stent groups with near 0 wt %, 0.2 wt %, 0.55 wt %, 1 wt % and about 3 wt % of LLA in PLLA were studied and tracked over a four month period. In these studies, the radial strength and stent integrity were tracked. Table 5 summarizes the observed change in radial strength and mechanical integrity after radial strength testing for the different groups. As shown in Table 5, for near 0 wt %, 0.2 wt %, and 0.55 wt % LLA, the radial strength is maintained up to more than 4 months and there were no fractures observed up to more than 4 months. For 1 wt % LLA, the radial strength showed a consistent decrease between about 1½ months to about 3 months. The drop in radial strength might occur sooner in vivo. Additionally, the significant fractures at only 42 days indicate an early loss of radial strength and mechanical integrity. These results indicate a stent with greater than 1 wt % LLA might not be a great candidate for coronary or peripheral applications. The drop in radial strength and significant fractures in the stent with about 3 wt % LLA indicate that a PLLA stent with this concentration is totally unsuitable.

TABLE 5

Radial strength and mechanical integrity of PLLA stents with different LLA monomer content.

| LLA content (wt %) | Radial strength | Mechanical integrity |
|---|---|---|
| 0.05 | maintained up to more than 4 months (126 days) | no fractures at up to more than 4 months (126 days) |
| 0.2 | maintained up to more than 4 months (126 days) | no fractures at up to more than 4 months (126 days) |
| 0.55 | maintained up to more than 4 months (126 days) | no fractures at up to more than 4 months (126 days) |

TABLE 5-continued

Radial strength and mechanical integrity of PLLA stents with different LLA monomer content.

| LLA content (wt %) | Radial strength | Mechanical integrity |
|---|---|---|
| 1.0 | consistent decrease between ~1½ months to about 3 months | stent segments in pieces observed at 42 days |
| ~3 | consistent decrease starting at about 2 weeks | stent segments in pieces observed at 14 days |

Preclinical in vivo (animal) results for stent groups with a 0 wt %, 0.1 wt %, 0.4 wt % LLA, ca. 0.6 wt % LLA, 1 wt % LLA, and 3.8 wt % LLA have been obtained for up to 28 days after implantation. For stents with 0.4 wt % LLA and ca. 0.6% there were no fractures observed at 28 days after implantation. For stents with 1 wt % LLA, fractures were observed at 28 days after implantation. For stents with 3.8 wt % LLA, there were significant fractures at only 7 days and the stent broke into pieces after 28 days.

It has been observed by the inventor that forming a PLLA tube intended to have between 0.05-0.5 wt % LLA by mechanical blending of the requisite amount of LLA in PLLA fails to result in tubes with uniform blending of the LLA. Large variations in LLA concentration between stents formed from tubes in this manner were observed.

In some embodiments, the LLA can be mixed with PLLA using solvent blending. Solvent blending may include making a master batch of PLLA and LLA mixture with concentrations of LLA larger than the target concentration. The master batch is made by dissolving LLA and PLLA in a solvent such as chloroform. The chloroform is evaporated to form the master batch which is a uniform mixture of PLLA and LLA. The master batch is then mixed by melt processing, such as in an extruder, with a sufficient amount of PLLA to obtain the target LLA concentration. The method is illustrated by the following example:

Step 1: Dissolve 2 g LLA monomer and 8 g PLLA in 400 ml chloroform
Step 2: Evaporate chloroform to form uniform mixture of PLLA and LLA with 25 wt % LLA.
Step 3: Blend 25 wt % LLA mixture in extruder with 390 g of PLLA to obtain 0.5 wt % LLA in PLLA.

In other embodiments, LLA can be mixed with PLLA using spray coating. The spray coating can include preparing a uniform mixture of LLA in PLLA includes dissolving LLA in a solvent such as methanol to form a solution and spraying the solution on PLLA pellets. The solvent is removed leaving the LLA deposited on the PLLA pellets. The PLLA pellets are melt processed, in an extruder, for example, to form tubes with the target concentration of LLA in PLLA. The method is illustrated by the following example:

Step 1: Dissolve 5 g LLA in 100 ml anhydrous methanol to form solution.
Step 2: Spray solution onto 1 kg of PLLA pellets and stir.
Step 3: Place pellets in vacuum oven to remove solvent.
Step 4: Place pellets in extruder and form tube with 0.5 wt % of LLA.

At low concentrations of LLA (e.g., less than 1 wt %), melt blending can result in nonuniform mixing of LLA monomer and PLLA polymer. Specifically, phase separation of LLA from PLLA occurs and has been observed by the inventors. The phase separation is likely due to the large density variation between LLA monomer and PLLA. The nonuniform distribution may result in variations in the degradation rate of the final products made from the PLLA.

To address this, further embodiments of making a PLLA material with uniform LLA monomer content for making a stent or other medical device involves control of polymerization conditions during PLLA synthesis, control of post-processing conditions, or both. Such embodiments can provide PLLA pellets for processing into a stent with uniformly distributed LLA monomer at both low and high concentrations of LLA, i.e., from 0.01 wt % to 5 wt %.

In conventional medical grade PLLA polymer material synthesis, it is a basic goal or requirement to obtain high purity PLLA resin with very low LLA monomer content. Polymerization is performed with the goal to minimize the LLA monomer content in the final product since it is generally believed that large amount of monomers may cause irritation in vivo for some applications. Also, it is generally common sense that any impurities may complicate the downstream processes depending on the applications. The polymerization temperature and reaction time are two variables of the polymerization process that significantly influence the conversion of LLA to PLLA, and thus the LLA content in a PLLA product.

Figure 4:
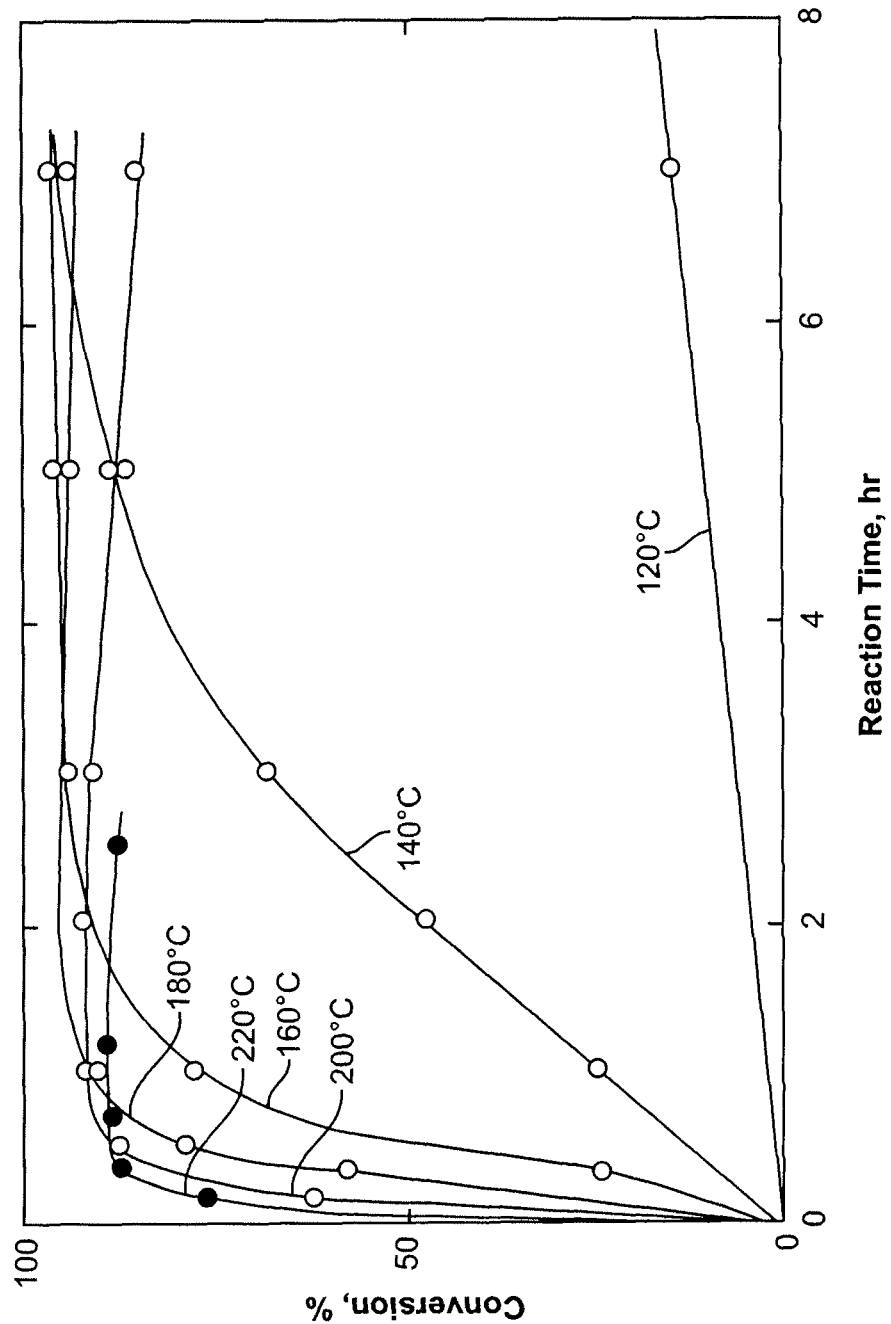
FIG. 4 depicts the dependence of the monomer conversion on the reaction time for bulk polymerization of L-lactide at different temperatures.

An example of PLLA synthesis is ring-opening polymerization of L-lactide in the bulk phase using stannous octoate (tin(II1 2-ethylhexanoate) as catalyst. (S. Hyon et al., Biomaterials 16 (1997) 1503-1508) Hyon et al. have presented the monomer conversion of PLLA as a function of time for polymerizations carried out over a temperature range 120° C. to 220° C. FIG. 4 (FIG. 4 of Hyon et al.) depicts the dependence of the monomer conversion on the reaction time for bulk polymerization of L-lactide at different temperatures (catalyst=0.05 wt %). FIG. shows the LLA monomer conversion to the resulting PLLA increases with time in an initial stage of polymerization at all temperatures. In this initial stage, the conversion of the resultant polymers exhibits almost a linear increase up to the monomer conversion of about 80%. In later stages, or longer reaction times, there is a gradual decrease in the monomer conversion which becomes more pronounced at higher temperatures, i.e., above 180° C.

In order to meet the requirement of low LLA monomer content, polymerization is conventionally performed at relatively low temperatures (lower than 180° C., preferably 140-160° C.) with short reaction times (less than 16 h). The lower temperatures and short reaction times reduce or prevent depolymerization that regenerates monomers. Sometimes the reaction temperature at a later polymerization stage is lowered to eliminate any depolymerization.

In general, polymerization temperatures for PLLA are between 120-180° C., preferably, 140-160° C. The molecular weight of the product is also affected by the temperature and reaction time, but is also controlled by the monomer/initiator ratio. Typical initiators are alcohols like dodecanol or hexanol. To obtain a PLLA product with weight average molecular weight between 200 to 600 kg/mole, a monomer/initiator molar ratio of about 1500:1 to 4000:1 (molar) may be used. Additionally, a monomer/catalyst weight ratio of between 1000:1 to 2000:1 (weight) is used. After polymerization, the final product which is cut into quite small pellets, for example, a pellet can be about 0.1 g.

Additionally, residual monomer content is reduced by subjecting the polymer to post-processing that extracts monomer from the synthesized polymer. There are several monomer extraction post-processing methods that are used such as solvent extraction, supercritical $CO_2$ extraction, and vacuum/high temperature extraction. In solvent extraction, the polymer is soaked in a solvent for the monomer which is a non-solvent for polymer. In $CO_2$ extraction, the PLLA material is exposed to supercritical carbon dioxide which extracts LLA monomer from the material. In vacuum/high temperature extraction, a PLLA sample is exposed to temperatures in a range between 140-160° C. at very low pressures, less than 0.1 atm. There are several process variables in each of these processes that influence the degree of monomer extraction. However, the primary variable is time of exposure to the process. The longer the exposure, the higher the removal of monomer.

Extraction solvents for extracting LLA from PLLA include methanol, ethanol etc, which is solvent for LLA but poor or non-solvent for PLLA. The amount extracted is a function of soaking time in the solvent. Different soaking times result in final products with different monomer content. The higher the soaking time, the higher the removal of the monomer and the lower the monomer content of the resulting product. Due to the small size of the pellets, the extraction results in uniform content of monomer in the pallet. As an example, for a starting LLA monomer concentration of 5 wt %, the exposure time necessary to get a target monomer concentration less than 0.1% in solvents such as methanol may be at least 24 h.

Thus, conventionally, polymerization is performed to result in a product with a monomer content as low as possible. Additionally, monomer extraction conventionally is applied to remove all monomer or as much as practically possible from a polymer.

In the various aspects disclosed, polymerization, alone or in combination with post-processing extraction, is performed to deliberately result in a PLLA polymer material with a LLA monomer content higher than conventionally desirable with the object to provide or control the degradation rate of a stent made from the PLLA material. Additionally, post-processing monomer extraction may be applied either alone or in combination with polymerization to provide a PLLA product with such monomer content. In some embodiments, the target LLA monomer concentration resulting from polymerization, post-processing, or both is between 0.01 to 2 wt %, 0.05 to 5 wt %, 0.05 to 2 wt %, 0.05 to 1 or wt % or 0.5 to 2 wt %.

In other embodiments, the target LLA monomer concentration is less than 2 wt %, less than 1 wt %, less than 0.9 wt %, less than 0.7 wt %, less than 0.5 wt %, less than 0.4 wt %, less than 0.3 wt %, less than 0.2 wt %, or less than 0.1 wt % of LLA monomer. In additional embodiments, the target LLA monomer concentration is 0 and 1 wt % LLA, 1-2 wt % LLA, 2-3 wt % LLA.

In certain embodiments of the invention, the target content of LLA of the PLLA product is controlled through control of the post-processing. In particular, the LLA monomer content is controlled through the exposure time of the PLLA pellets in a process such as solvent extraction, supercritical $CO_2$ extraction, or vacuum/high temperature extraction. For solvent extraction, the exposure time corresponds to the time the PLLA pellets are soaked in the extraction solvent. For supercritical $CO_2$ extraction, the exposure time corresponds to the time of exposure of the PLLA pellets to supercritical $CO_2$ at the extraction conditions. For vacuum/high temperature extraction, the exposure time corresponds to the time of exposure of the PLLA pellets to the vacuum/high temperature extraction conditions.

In these embodiments, a PLLA polymer material is obtained that has a relatively high LLA monomer content. The LLA content may be, for example, greater than 3 wt %, greater than 4 wt %, or greater than 5 wt % LLA. The PLLA is exposed to the extraction conditions for a target exposure time during which LLA is extracted from the PLLA and then extraction is terminated. Terminating extraction can correspond to removing the PLLA from the solvent or extraction chamber or changing the conditions of an extraction chamber to conditions that do not extract LLA. In other embodiments, the extraction can be performed in stages in which extraction can be terminated before reaching a target LLA content and then exposed one or more additional times until a target LLA content is reached.

After extraction is completed, the PLLA has a target LLA content due to the extraction of the LLA from the exposure. The target exposure time is the exposure time that results in a target LLA monomer content, ranges of which are provided above, in the PLLA polymer material. The target exposure time can be determined from exposure of a plurality of PLLA samples at different exposure times. For example, an initial exposure time for a sample can be selected and then additional samples can be exposed at progressively higher exposure times until an exposure is reached that provides the target LLA monomer content.

In additional embodiments, a PLLA material with the target LLA content is obtained through control of conditions of post-processing monomer extraction in combination with control of polymerization. In such embodiments, a PLLA polymer material with relatively high monomer content is prepared first by control of polymerization conditions. PLLA polymer material refers to PLLA polymer, LLA monomer, and any other impurities or residue.

Making a PLLA polymer material from polymerization with such LLA monomer content can be accomplished with various combinations of reaction times and temperatures. The PLLA polymer material can be made with a LLA monomer content of, for example, greater than 3 wt %, greater than 4 wt %, or greater than 5 wt % LLA. In one embodiment, the relatively high LLA monomer content can be achieved with a relatively low reaction temperature and short reaction time. In another embodiment, the relatively high LLA monomer content can be achieved with high reaction temperature and relatively long reaction time. In the third embodiment, the relatively high LLA monomer content can be achieved in two steps. During a first stage where a high consumption of LLA is achieved with a relatively low reaction temperature and long enough reaction time, and then increasing reaction temperature at a late polymerization stage and prolonging reaction time sufficiently to obtain a desired LLA monomer content. For example, the reaction temperature can be less than 160° C. for a first stage with a reaction time of less than 20 h. The LLA monomer content at the end of this first stage can be lower than 1%, lower than 0.5%, or lower than 0.1%. The first stage is then followed by a second stage with a temperature greater than 180° C. or 180-200° C. and a reaction time of more than 4 h. The LLA monomer content of the PLLA polymer material at the end of the second stage may be greater than 4 wt %, greater than 5 wt %, 5-7 wt %, 7-10 wt %, or greater than 10 wt %.

The PLLA polymer material at the end of the second stage with the relatively high monomer content can then be subjected to post-processing extraction to reduce the LLA content to a target LLA monomer content. The LLA monomer content can be reduced by the extraction to any value of the disclosed target LLA content ranges, or any value between 100 ppm to 5 wt %.

In further embodiments, a PLLA polymer material with the target LLA content can be made by a polymerization scheme that includes two stages. In the first stage, the polymerization has a relatively high conversion resulting in a PLLA material with a relatively low LLA monomer content. The relatively low LLA monomer content can be lower than the disclosed target LLA monomer content ranges or within such ranges. In the second stage, the reaction temperature is increased to cause depolymerization which increases the LLA monomer content to a target LLA monomer content.

For example, the conversion of the first stage polymerization can be greater than 98%, 99%, or 99.5%. The LLA monomer content at the end of the first stage may be less than 2%, 1%, or 0.5%. In the second stage, the depolymerization causes the LLA monomer content to increase to any range or any value in the disclosed ranges of the target LLA monomer content.

The resulting PLLA material from the depolymerization stage may then be used for making a stent without any post-processing extraction process to decrease the LLA monomer content. Optionally, post-processing extraction can be performed on the PLLA material to reduce the LLA monomer content further to a lower target LLA monomer content.

In the first stage, the polymerization that achieves the high conversion can be achieved using a variety of combinations of temperature and reaction times. The polymerization can be performed at a temperature or temperatures between 120-160° C., 125-150° C., or 140-150° C. The reaction time is sufficient to provide the high conversion that is desired, for example, the reaction time may be greater than 10 h, 15 h, 20 h, or more than 20 h. These reaction time ranges may correspond to any of the above temperature ranges. The reaction temperature for the second stage may be greater than 180° C., 180-200° C., or greater than 200° C. The reaction time is sufficient to increase the LLA monomer content to a target LLA monomer content. For example, the reaction time may be less than 6 h, less than 1 h, 1-2 h, 2-3 h, 3-4-h, or 4-6 h.

In additional embodiments, a PLLA material with a target LLA monomer content can be made by a polymerization reaction performed at a selected reaction temperature for a selected reaction time to results in the PLLA material with the target LLA content. In this embodiment, the polymerization reaction provides the PLLA material without further post-processing extraction of LLA monomer. Optionally, post-processing extraction can be performed on the PLLA material to reduce the LLA monomer content further to a lower target LLA monomer content. Embodiments include any temperature between 120-180° C. and any reaction time between 1 h and 100 h and any combination of these temperatures and reaction times that provides a PLLA polymer material with any of the ranges and values with in such ranges of the disclosed target LLA monomer content.

The selected reaction temperature and reaction time that provides a target LLA monomer content may be determined in at least two ways. One way is to fix a reaction temperature and perform the polymerization reaction at different reaction times to determine the reaction time that provides the target LLA monomer content at the selected reaction temperature. For example, a target LLA monomer content may be 0.5% wt % and a selected reaction temperature may be 140° C. The polymerization reaction may then be performed for reaction times between at least 6 h and 30 h. The selected reaction time is that which corresponds to the reaction time that provides the target LLA monomer content of 0.5 wt %.

Another way to determine the selected reaction temperature and reaction time that provides a target LLA monomer content is to fix a reaction time and perform the polymerization reaction at different reaction temperatures to determine the reaction temperature that provides the target LLA monomer content in the selected reaction time. For example, a target LLA monomer content may be 0.5 wt % and a selected reaction time may be around 20 h. The polymerization reaction may then be performed for reaction temperatures between at least 120 and 170° C. The selected reaction temperature is that which corresponds to the reaction temperature that provides the target LLA monomer content of 0.5 wt %. If the reaction time is too short, there may not provide the target LLA monomer content (see FIG. 4). Additionally, there is a lower limit of the LLA content at higher temperatures due to depolymerization (see FIG. 4).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a stent comprising:
    making PLLA polymer material having an LLA monomer content of greater than 4 wt % with a polymerization reaction of LLA monomers, wherein the polymerization reaction comprises two steps,
        wherein in a first step the polymerization reaction is performed at a reaction temperature less than 160° C. for a first period of time to obtain a PLLA material of the first step and,
        wherein in a second step the polymerization reaction of the PLLA material of the first step is performed at a temperature between 180-200° C. to obtain the PLLA polymer material having the LLA monomer content of more than 4 wt %,
    processing the PLLA polymer material to extract some of the LLA monomer to reduce the LLA monomer content to no more than 2 wt %; and
    making a polymeric stent body from the processed PLLA polymer material.

2. The method of claim 1, wherein the processing comprises treating the synthesized PLLA with a solvent that reduces the monomer content.

3. The method of claim 1, wherein the processing comprises a liquid solvent extraction process, wherein exposure of the PLLA polymer material extracts LLA monomer from the material.

4. The method of claim 1, wherein the processing is selected from the group consisting of supercritical $CO_2$ extraction and vacuum/high temperature extraction.

5. The method of claim 1, wherein the processed PLLA material has an LLA monomer content of 0.01-2 wt %.

6. The method of claim 1, wherein the processed PLLA material has an LLA monomer content of 0.01-1 wt %.

7. The method of claim 1, wherein the processed PLLA material has an LLA monomer content of 0.01-0.5 wt %.

8. The method of claim 1, wherein the processed PLLA material has an LLA monomer content of 0.01-2 wt %.

9. A method of fabricating a stent comprising:
    making a PLLA polymer material with a polymerization reaction of LLA monomer, wherein the PLLA polymer material has a LLA monomer content of less than 0.5 wt %;
    increasing a reaction temperature of the PLLA polymer material to cause depolymerization which increases the monomer content to a target LLA monomer content of between less than 0.5 to 2 wt % of the PLLA; and
    making a stent body from the PLLA polymer material with the increased monomer content.

10. The method of claim 9, wherein the temperature is increased to a target temperature and the reaction time is adjusted to obtain the target monomer content.

11. The method of claim 9, wherein the reaction temperature is increased from temperature in a range of 120-140° C. to a temperature in a range above 180° C.

12. The method of claim 9, wherein the PLLA material after the depolymerization is used for making a stent without any post-processing extraction process to decrease the LLA monomer content.

13. The method of claim 1, wherein a crystallinity of the polymeric stent body is 30 to 50%.

* * * * *